(12) United States Patent
Finkam et al.

(10) Patent No.: US 7,030,276 B2
(45) Date of Patent: Apr. 18, 2006

(54) PROCESS FOR PREPARING 2-[(DIMETHYLAMINO)-METHYL]-1-(3-METHOXYPHENYL)CYCLOHEXANOL

(75) Inventors: Michael Finkam, Aachen (DE); Bernhard Akteries, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/052,776

(22) Filed: Feb. 9, 2005

(65) Prior Publication Data

US 2005/0215821 A1 Sep. 29, 2005

Related U.S. Application Data

(63) Continuation-in-part of application No. PCT/EP03/08746, filed on Aug. 7, 2003.

(30) Foreign Application Priority Data

Aug. 9, 2002 (DE) ................................ 102 36 510

(51) Int. Cl.
*C07C 209/00* (2006.01)

(52) U.S. Cl. ..................... 564/424; 564/304; 564/437; 564/443

(58) Field of Classification Search ................ 564/304, 564/424, 437, 443

See application file for complete search history.

(56) References Cited

U.S. PATENT DOCUMENTS 6,399,829 B1   6/2002   Jarvi
6,469,213 B1   10/2002  Schickaneder

FOREIGN PATENT DOCUMENTS

WO   99 03820   1/1999
WO   99 61405   12/1999

*Primary Examiner*—Samuel Barts
(74) *Attorney, Agent, or Firm*—Crowell & Moring LLP

(57) ABSTRACT

A process for preparing 2-[(dimethylamino)methyl]-1-(3-methoxyphenyl)cyclohexanol with high stereoselectivity and high yield by reacting 2-[(dimethylamino)methyl]-cyclohexanone in a Grignard reaction with a Grignard compound of 3-bromoanisole in a suitable solvent and in the presence of an inorganic lithium salt and an α,ω-dialkoxyalkane.

14 Claims, No Drawings

PROCESS FOR PREPARING 2-[(DIMETHYLAMINO)-METHYL]-1-(3-METHOXYPHENYL)CYCLOHEXANOL

CROSS REFERENCE TO RELATED APPLICATIONS

This application is a continuation of International Patent Application No. PCT/EP03/08746, filed Aug. 7, 2003, designating the United States of America, and published in German as WO 2004/020390 on Mar. 11, 2004, the entire disclosure of which is incorporated herein by reference. Priority is claimed based on Federal Republic of Germany patent application no. DE 102 36 510.5, filed Aug. 9, 2002.

BACKGROUND OF THE INVENTION

The invention provides a process for the preparation of 2-[(dimethylamino)methyl]-1-(3-methoxyphenyl)cyclohexanol with a high stereoselectivity for the trans form from the enantiomers (1R,2R)- and (1S,2S)-2-[(dimethylamino)methyl]-1-(3-methoxyphenyl)cyclohexanol.

Tramadol, which is called "trans isomer" for historical reasons and comprises the trans form from the enantiomers (1R,2R)- and (1S,2S)-2-[(dimethylamino)methyl]-1-(3-methoxyphenyl)cyclohexanol, has an analgesic action and is therefore employed as an analgesic.

As is known, 2-[(dimethylamino)methyl]-1-(3-methoxyphenyl)-cyclohexanol can be prepared by a Grignard reaction of 2-[(dimethylamino)methyl]cyclohexanone and the Grignard compound of 3-bromoanisole. Both the cis and the trans form are formed in this reaction.

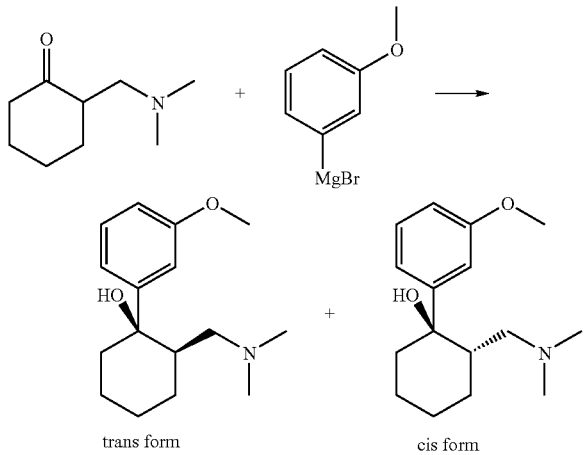

The trans form, hereinafter referred to as the trans isomer, comprises the R,R and S,S enantiomers with the following two formulas:

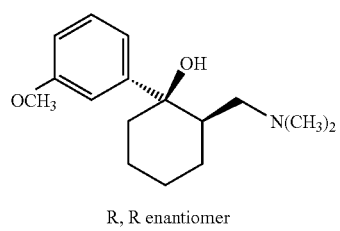

R, R enantiomer

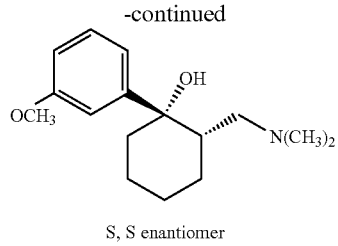

S, S enantiomer

The cis form, called cis isomer in the following, comprises the S,R and R,S isomers with the following two formulas:

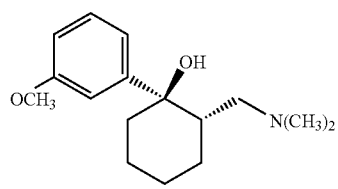

1R, 2S enantiomer

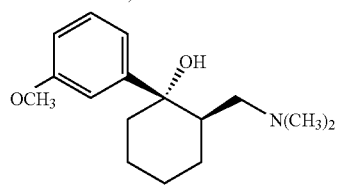

1S, 2R enantiomer

In the preparation of tramadol with the aid of a Grignard reaction, a highest possible yield of the trans isomer, the tramadol Grignard base, is aimed for. In this regard, it is already known that the choice of solvents and/or presence of salt additives can influence the diastereoselectivity of the Grignard reaction.

According to the teaching of WO99/61405, a shift in the trans:cis isomer ratio from approx. 80:20 to 90:10 in the preparation of 2-[(dimethylamino)methyl]-1-(3-methoxyphenyl)cyclohexanol by the use of amine or ethers is described. However, the yield achieved is in some cases only comparable to a reaction without additions, and in some cases even significantly poorer.

Savelyev et al. (International Conference on Natural Products and Physiologically Active Substances, Novosibirsk, 30 Nov.–6 Dec. 1998, poster) also describe an increase in the diastereoselectivity in the preparation of 2-[(dimethylamino)methyl]-1-(3-methoxyphenyl)cyclohexanol by addition of dioxanes, but the total yield of cis and trans isomer of 2-[(dimethylamino)methyl]-1-(3-methoxyphenyl)cyclohexanol is adversely affected.

SUMMARY OF THE INVENTION

It was therefore an object of the invention to provide an improved process for preparing 2-[(dimethylamino)methyl]-1-(3-methoxyphenyl)-cyclohexanol.

Another object of the invention was to provide a process for preparing 2-[(dimethylamino)methyl]-1-(3-methoxyphenyl)cyclohexanol with both a high stereoselectivity for the trans isomer and high yields.

These and other objects have been achieved in accordance with the present invention by providing a process for preparing 2-[(dimethylamino)methyl]-1-(3-methoxyphenyl)cyclohexanol comprising reacting 2-[(dimethylamino)methyl]cyclohexanone in a Grignard reaction with a Grignard compound of 3-bromoanisole in a suitable solvent and in the presence of an inorganic lithium salt and an $\alpha,\omega$-di-$(C_{1-3})$-alkoxy-$(C_1-C_3)$-alkane.

The invention therefore provides a process for the preparation of 2-[(dimethylamino)methyl]-1-(3-methoxyphenyl)cyclohexanol by a Grignard reaction of 2-[(dimethylamino)methyl]cyclohexanone with the Grignard compound of 3-bromoanisole, working up of the reaction mixture and optionally purification of the corresponding cyclohexanol, characterized in that 2-[(dimethylamino)methyl]cyclohexanone and the Grignard compound of 3-bromoanisole are reacted in a suitable solvent in the presence of an inorganic lithium salt and an $\alpha,\omega$-di-$(C_{1-3})$-alkoxy-$(C_1-C_3)$alkane.

Preferably, the Grignard compound of 3-bromoanisole is initially introduced into the reaction vessel in a suitable solvent, an inorganic lithium salt and a corresponding dialkoxy compound are added to the solution, and the mixture is optionally subsequently stirred and then reacted with 2-[(dimethylamino)methyl]cyclohexanone.

The solution of the Grignard compound of 3-bromoanisole is preferably prepared by reaction of 3-bromoanisole with magnesium in a suitable solvent, particularly preferably directly before the reaction with the Mannich base.

The inorganic lithium salt is preferably employed in amounts of 0.5–1 equivalent, based on the 3-bromoanisole. Preferably, a lithium halide, particularly preferably lithium chloride, is used as the inorganic lithium salt.

The dialkoxyalkane is preferably added in amounts of 20–120 vol. %, based on the abovementioned solvent. 1,2-Dimethoxyethane is preferably used as the dialkoxyalkane.

The reaction of magnesium and 3-bromoanisole to give the Grignard compound is preferably carried out at a temperature of 50–100° C.

An organic solvent is preferably used as the solvent for the Grignard compound, particularly preferably tetrahydrofuran.

The additions of the inorganic lithium salt, the dialkoxyalkane and 2-[(dimethylamino)methyl]cyclohexanone to the solution of the Grignard compound of 3-bromoanisole and the reaction are preferably carried out at a temperature of 0–60° C., particularly preferably at a temperature of 15–35° C.

In order to work up the reaction mixture, the reaction mixture is preferably introduced into cooled aqueous ammonium chloride solution and, after separation of the phases, the organic phase is freed from the solvent.

Surprisingly, process according to the invention makes it possible to improve both the yield of the Grignard base and the stereoselectivity in favor of the desired trans isomer, i.e. to increase the trans:cis isomer ratio significantly with a high yield of the Grignard base.

The mixture of the diastereomeric Grignard bases obtained with the process according to the invention can be processed in a known manner, for purification and, in particular, separation of the trans isomer from the cis isomer, into the hydrochloride by reaction with hydrochloric acid and the tramadol hydrochloride can preferably be recrystallized from dioxane/water.

The desired trans isomer can of course be isolated by any conventional separation method from the Grignard base of the trans and cis isomer obtained according to the invention.

The tramadol HCl obtained according to the invention can be employed as an analgesically active compound.

EXAMPLES

Example 1

A) Grignard Reaction

The reaction was carried out in a 90 liter tank. 1.46 kg (60 moles) of magnesium filings were initially introduced into the reaction vessel and were heated thoroughly at 120° C. After addition of 18 liters of tetrahydrofuran, the mixture was heated to an internal temperature of 55° C., and 0.5 kg of 3-bromoanisole was added dropwise to start the reaction. After the Grignard reaction had started, a further 10.73 kg (in total: 11.23 kg; 60 moles) of 3-bromoanisole were added dropwise, and the mixture was subsequently stirred.

The reaction product was then cooled to 25° C., 1.91 kg (45 moles; 0.75 equivalents, based on the 3-bromoanisole) of lithium chloride and 18 liters of dimethoxyethane were added, and the mixture was subsequently stirred for 30 minutes. 10.25 kg (66 moles) of 2-[(dimethylamino)methyl]-cyclohexanone were then added dropwise over the course of 2 hours, the internal temperature being kept below 30° C. After the addition, the mixture was subsequently stirred.

The reaction mixture was introduced slowly into a cooled ammonium chloride solution of 7.80 kg ammonium chloride in 28.5 liters of water, and the mixture was subsequently stirred for 0.5 hour. After separation of the phases, the aqueous phase was extracted several times with tetrahydrofuran. The organic phases were combined and filtered over magnesium sulfate. The solvent was then removed in vacuo, a red-brown coloured crude product of the cis and trans isomer of 2-[(dimethylamino)methyl]-1-(3-methoxyphenyl)cyclohexanol being obtained.

Yield: 10.8 kg (68% of the theoretical yield, HPLC) trans/cis isomer ratio: 92% :8%

B) Hydrochloride Precipitation 1 kg of the crude product containing the cis and trans isomers obtained according to A) was dissolved in ether, and dry hydrogen chloride was added. The trans isomer of the resulting hydrochloride of 2-[(dimethylamino)methyl]-1-(3-methoxyphenyl)cyclohexanol which formed was separated practically completely from the cis isomer by recrystallization from dioxane/water.

Yield: 76% of the theoretical yield

Comparison Example 1

A) Grignard Reaction

The reaction was carried out in a 90 liter tank. 1.46 kg (60 moles) of magnesium filings were initially introduced into the reaction vessel and were heated thoroughly at 120° C. After addition of 18 liters of tetrahydrofuran, the mixture was heated to an internal temperature of 55° C., and 0.5 kg of 3-bromoanisole was added dropwise to start the reaction. After the Grignard reaction had started, a further 10.73 kg (in total: 11.23 kg; 60 moles) of 3-bromoanisole were added dropwise, and the mixture was subsequently stirred.

The reaction product was then cooled to 25° C., 1.91 kg (45 moles; 0.75 eqivalents, based on the 3-bromoanisole) of lithium chloride and 14.7 liters of tetrahydrofuran were added, and the mixture was subsequently stirred for 30 minutes. 10.25 kg (66 moles) of 2-[(dimethylamino)methyl]-cyclohexanone were then added dropwise over the course of 2 hours, while the internal temperature was kept below 30° C. When the addition was complete, the mixture was subsequently stirred.

The reaction mixture was introduced slowly into a cooled ammonium chloride solution of 7.80 kg of ammonium chloride in 28.5 liters of water, and the mixture was subsequently stirred for 0.5 hour. After separation of the phases, the aqueous phase was extracted several times with tetrahydrofuran. The organic phases were combined and filtered over magnesium sulfate.

The solvent was then removed in vacuo, and a red-brown colored crude product containing the cis and trans isomers of 2-[(dimethylamino)methyl]-1-(3-methoxyphenyl)cyclohexanol was obtained.

Yield: 10.8 kg (68% of the theoretical yield, HPLC) trans/cis isomer ratio: 83% :17%

B) Hydrochloride Precipitation 1 kg of the crude product containing the cis and trans isomers obtained according to A) was dissolved in ether, and dry hydrogen chloride was added. The trans isomer of the resulting hydrochloride of 2-[(dimethylamino)methyl]-1-(3-methoxyphenyl)cyclohexanol which formed was separated from the cis isomer by recrystallization from dioxane/water.

Yield: 60% of the theoretical yield

Example 2 and Comparison Examples 2 and 3

Further experiments were carried out in accordance with Example 1 and Comparison Example 1 with and without lithium chloride or dimethoxyethane. The amounts of the reaction components and additives are shown in the following Table 1 together with an overview for Example 1 and Comparison Example 1.

TABLE 1

|  | 3-Br-anisole and magnesium moles | 2-[(Dimethyl-amino)methyl]-cyclohexanone moles | THF ml | DME ml | LiCl Moles | Yield % | Isomer ratio trans % | cis % |
|---|---|---|---|---|---|---|---|---|
| Example 1 | 60 | 66 | 18,000 | 18,000 | 45 | 68 | 92 | 8 |
| Comparison example 1 | 60 | 66 | 32,700 | 0 | 45 | 68 | 83 | 17 |
| Example 2 | 0.45 | 0.50 | 135 | 60 | 0.45 | 70 | 92 | 8 |
| Comparison example 2 | 0.45 | 0.50 | 135 | 60 | 0 | 53 | 84 | 16 |
| Comparison example 3 | 0.45 | 0.50 | 135 | 0 | 0.45 | 70 | 87 | 13 |

THF = tetrahydrofuran
DME = 1,2-dimethoxyethane

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A process for preparing 2-[(dimethylamino)methyl]-1-(3-methoxyphenyl)cyclohexanol, said process comprising reacting 2-[(dimethylamino)methyl]cyclohexanone in a Grignard reaction with a Grignard compound of 3-bromoanisole in a suitable solvent and in the presence of an inorganic lithium salt and an α,ω-di-($C_{1-3}$)-alkoxy-($C_1$–$C_3$)-alkane.

2. A process according to claim 1, further comprising working up the reaction mixture, and thereafter purifying obtained 2-[(dimethylamino)methyl]-1-(3-methoxyphenyl)cyclohexanol.

3. A process according to claim 1, wherein the Grignard compound of 3-bromoanisole is initially introduced into the reaction vessel in solution in a suitable solvent; an inorganic lithium salt and an α,ω-di-($C_{1-3}$)-alkoxy-($C_1$–$C_3$)alkane are added to the solution, and then the 2-[(dimethylamino)methyl]cyclohexanone is added to the mixture and reacted with the Grignard compound.

4. A process according to claim 3, wherein the solution of the Grignard compound of 3-bromoanisole is prepared directly prior to the Grignard reaction by reacting 3-bromoanisole and magnesium in a suitable solvent.

5. A process according to claim 1, wherein the lithium salt is present in an amount of from 0.5 to 1 equivalent, based on the 3-bromoanisole.

6. A process according to claim 1, wherein the lithium salt is lithium chloride.

7. A process according to claim 1, wherein the α,ω-di-($C_{1-3}$)-alkoxy-($C_1$–$C_3$)-alkane is present in an amount of from 20 to 120 vol. %, based on the solvent.

8. A process according to claim 1, wherein the α,ω-di-($C_{1-3}$)-alkoxy-($C_1$–$C_3$)-alkane is 1,2-dimethoxyethane.

9. A process according to claim 1, wherein the solvent is tetrahydrofuran.

10. A process according to claim 1, wherein the Grignard reaction is carried out at a temperature of from 0 to 60° C.

11. A process according to claim 10, wherein the Grignard reaction is carried out at a temperature of from 15 to 35° C.

12. A process according to claim 4, wherein the Grignard compound is prepared at a temperature of from 50 to 100° C.

13. A process according to claim 2, wherein the reaction mixture is worked up by introducing the reaction mixture into cooled ammonium chloride solution, separating organic and inorganic phases, and freeing the organic phase from solvent.

14. A process according to claim 2, for preparing tramadol HCl wherein tramadol, which is in the form of a trans isomer, is separated by treating the worked-up reaction mixture with hydrochloric acid to form a hydrochloride, and recrystallizing the hydrochloride from a dioxane/water mixture.

* * * * *